United States Patent [19]

Cleary et al.

[11] Patent Number: 4,906,463
[45] Date of Patent: Mar. 6, 1990

[54] TRANSDERMAL DRUG-DELIVERY COMPOSITION

[75] Inventors: Gary W. Cleary, San Mateo; Samir Roy, Redwood City, both of Calif.

[73] Assignee: Cygnus Research Corporation, Redwood City, Calif.

[21] Appl. No.: 179,423

[22] Filed: Apr. 8, 1988

Related U.S. Application Data

[63] Continuation-in-part of Ser. No. 79,801, Jul. 30, 1987, abandoned, which is a continuation-in-part of Ser. No. 41,793, Apr. 23, 1987, abandoned, which is a continuation-in-part of Ser. No. 945,356, Dec. 22, 1986, abandoned.

[51] Int. Cl.$^4$ .................. A61K 31/56; A61K 31/74; A61K 31/445
[52] U.S. Cl. .................................. 424/78; 514/182; 514/329; 514/785; 514/947
[58] Field of Search ............... 514/552, 967, 785, 182, 514/329; 424/78

[56] References Cited

U.S. PATENT DOCUMENTS

| 3,426,754 | 2/1969 | Bierenbaum et al. | 128/156 |
|---|---|---|---|
| 3,486,968 | 12/1969 | Mater | 161/190 |
| 3,645,835 | 2/1972 | Hodgson | 161/146 |
| 3,685,734 | 8/1972 | Paciorek et al. | 239/56 |
| 3,797,494 | 3/1974 | Zaffaroni | 128/268 |
| 3,849,238 | 11/1974 | Gould et al. | 161/159 |
| 4,060,084 | 11/1977 | Chandrasekaran et al. | 128/260 |
| 4,367,732 | 1/1983 | Poulsen et al. | 128/156 |
| 4,379,454 | 4/1983 | Campbell et al. | 604/897 |
| 4,435,180 | 3/1984 | Leeper | 604/896 |
| 4,438,139 | 3/1984 | Keith et al. | 424/28 |
| 4,452,845 | 6/1984 | Lloyd et al. | 428/220 |
| 4,460,371 | 7/1984 | Abber | 604/897 |
| 4,460,372 | 7/1984 | Campbell et al. | 604/897 |
| 4,510,197 | 4/1985 | Shah | 128/156 |
| 4,552,751 | 11/1985 | Inaba et al. | 604/196 |
| 4,559,054 | 12/1985 | Bruck | 128/156 |
| 4,568,343 | 2/1986 | Leeper et al. | 604/896 |
| 4,588,580 | 5/1986 | Gale et al. | 424/21 |
| 4,600,001 | 7/1986 | Gilman | 128/156 |
| 4,623,346 | 11/1986 | von Bittera et al. | 604/897 |
| 4,638,797 | 1/1987 | Merrill et al. | 128/156 |
| 4,645,502 | 2/1987 | Gale et al. | 604/896 |
| 4,655,768 | 4/1987 | Martecki et al. | 604/897 |
| 4,675,009 | 6/1987 | Hymes et al. | 604/304 |
| 4,687,481 | 8/1987 | Nuwayser | 604/897 |

FOREIGN PATENT DOCUMENTS

| 0171742 | 2/1980 | European Pat. Off. |
|---|---|---|
| 0020117 | 12/1980 | European Pat. Off. |
| 59-84817 | 11/1982 | Japan . |
| 61133114 | 1/1984 | Japan . |

OTHER PUBLICATIONS

Augnst et al.–International Journal of Pharmaceutics 33 (1986), 225–234.
Chemical Abstracts 88:55014e (Mayer et al.), 1978.
Nitto Electric Industrial Co., (1985) Chemical Abstracts 102 (18):354, Abstract No. 154817h.

Primary Examiner—Leonard Schenkman
Attorney, Agent, or Firm—Irell & Manella

[57] ABSTRACT

A solid state, resilient laminated composite for administering a drug transdermally consisting of a multiplicity of spaced structural laminas of a resilient elastomer, one of which forms the top of the composite, a viscoelastic hydrophobic polymer lamina containing propylene glycol monolaurate interposed between each structural lamina and a pressure-sensitive adhesive lamina that provides the basal surface of the composite and consists of a blend of a pressure-sensitive adhesive, drug and propylene glycol monoalaurate.

12 Claims, 2 Drawing Sheets

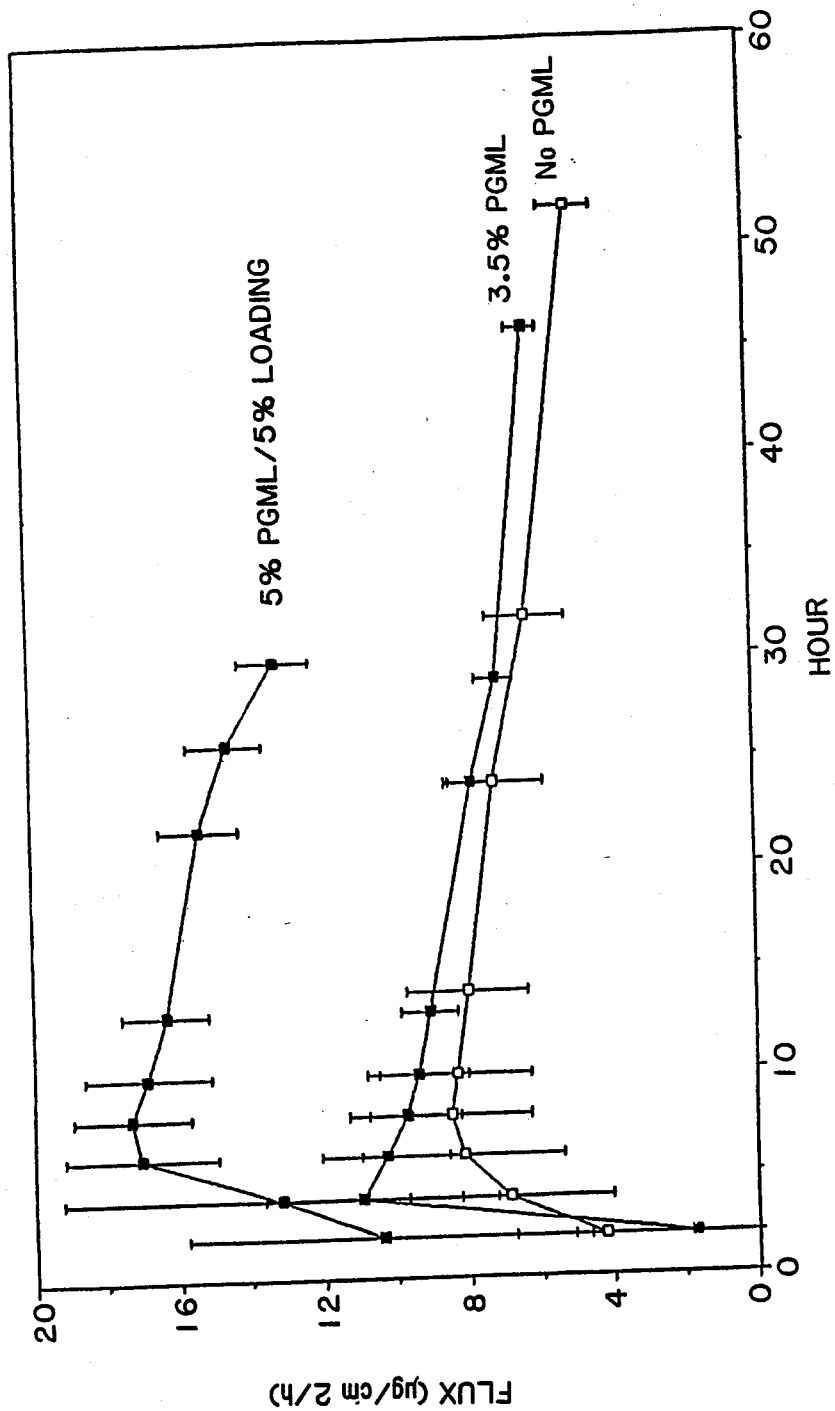

TRANSDERMAL DRUG-DELIVERY COMPOSITION

CROSS-REFERENCE TO RELATED APPLICATIONS

This application is a continuation-in-part of copending U.S. patent application Ser. No. 079,801, filed July 30, 1987 which in turn is a continuation-in-part of U.S. patent application Ser. No. 041,793, filed Apr. 23, 1987 which is a continuation-in-part of U.S. patent application Ser. No. 945,356, filed Dec. 22, 1986, all of which are now abandoned.

Technical Field

This invention is in the field of transdermal drug-delivery. More particularly it relates to a transdermal drug-delivery device in the form of a solid state laminated composite that is adapted to be adhered to the skin and that includes a multiplicity of spaced resilient structural laminas that provide the device with mechanical properties that enable the device to stretch in concert with the area of skin to which it is adhered and which facilitate its handling prior to application. One embodiment of the invention is particularly adapted for administering estradiol transdermally. Another is particularly adapted for administering fentanyl or fentanyl derivatives transdermally.

Background of the Invention

A variety of devices have been proposed or used for administering drugs transdermally. These devices are generally laminated composites that include a reservoir layer that contains the drug, a pressure-sensitive adhesive layer by which the device is attached to the skin, and a backing layer that forms the outer "skin" of the device. Depending upon the inherent permeability of the skin to a particular drug, the device may also include means for coadministering a percutaneous absorption enhancer or an element, such as a membrane interposed between the reservoir and the skin, that regulates the rate at which the drug and/or the enhancer is administered to the skin.

U.S. Pat. Nos. 4,379,454 and 4,460,372 describe a device for coadministering a drug and a percutaneous absorption enhancer transdermally. The drug is presented to the skin at a rate in excess of that which the skin is inherently capable of absorbing and the enhancer is presented to the skin at a substantially constant rate that is sufficient to permit the skin to pass therapeutic levels of drug to circulation. The device includes a membrane interposed between a drug-and enhancer-containing reservoir layer and a pressure-sensitive adhesive layer that regulates the rate at which the enhancer is presented to the skin. In the commercial estradiol embodiment of this device (marketed under the mark ES-TRADERM) the enhancer is ethanol and the estradiol-ethanol mixture is contained in the reservoir in a fluid form. Using such a form complicates the procedures for manufacturing the device and detracts from the ability to optimize certain physical characteristics of the device such as thickness, resiliency, and adhesiveness, that are associated with wearability.

Other patent publications relating to devices for administering estradiol transdermally are German Patent Publication Nos. 3 315 245 and 3 315 272, European Patent Publication Nos. 0013606 and 0040861 and U.S. Pat. No. 4,438,139.

Patent publications relating to transdermal delivery of opioids in general and fentanyl or fentanyl derivatives or analogs (sufentanil, carfentanil, lofentanil, and alfentanil) are EPA No. 0171742 and U.S. Pat. Nos. 4,588,580 and 4,626,539.

U.S. Pat. No. 4,435,180 describes a transdermal drug-delivery device comprising a body of a mixture of elastomer and drug, the body being in a form such as an arm or wrist band which inherently creates a compressive force when worn to keep the body firmly in contact with the skin.

The focus of much of the prior art relating to transdermal drug delivery has been on the release kinetics of the drug or enhancer from the device. Because of this the design of most prior devices has centered about the achievement of desired drug release kinetics, and, for the most part has ignored or given only secondary consideration to mechanical properties that enhance its wearability and cosmetic acceptability. In this regard, the present invention provides a transdermal drug-delivery device that provides acceptable drug release kinetics as well as resiliency, thinness and, when permitted, breathability.

DISCLOSURE OF THE INVENTION

The invention is a transdermal drug-delivery device in the form of a solid state laminated composite adapted to be adhered to a predetermined area of unbroken skin and having mechanical properties that enable it to expand and contract in concert with the normal expansion and contraction of said area of skin comprising:

(a) at least two spaced structural laminas of a resilient polymer, said laminas providing the composite with said mechanical properties;

(b) at least one lamina of a viscoelastic hydrophobic polymer optionally in which (i) a drug and/or (ii) an agent that enhances the solubility of the drug in the viscoelastic hydrophobic polymer and/or is a percutaneous absorption enhancer that increases the permeability of the skin to the drug is dispersed and at least partly dissolved, the viscoelastic hydrophobic polymer lamina being positioned between the structural laminas with the structural lamina(s) underlying the viscoelastic hydrophobic polymer lamina(s) providing no rate-controlling barrier to diffusion of drug and/or agent from the viscoelastic hydrophobic polymer lamina(s) to the skin; and (c) a lamina of a pharmaceutically acceptable pressure-sensitive adhesive optionally in which (i) said drug and/or (ii) said agent is dispersed and at least partly dissolved, one face of the pressure-sensitive adhesive lamina defining the basal surface of the composite and contacting and adhering to the area of unbroken skin when the device is in use, said pressure-sensitive adhesive lamina providing no rate-controlling barrier to diffusion of the drug and/or agent from the device to the skin, with the proviso that at least one of said viscoelastic hydrophobic polymer lamina(s) and said pressure-sensitive adhesive lamina contains the drug.

Prior to use the device also includes a release liner lamina that covers the basal surface of the pressure-sensitive adhesive lamina and is adapted to be removed from the device to expose the basal surface of the pressure-sensitive adhesive lamina.

In embodiments which involve a steroidal drug, such as estradiol, or certain opioids such as fentanyl and fentanyl analogs, it may be necessary that the device be a sufficient barrier to water vapor transmission to cause the area of skin to become hydrated and thus more permeable to the drug. In other embodiments involving drugs that do not require that the skin be hydrated, the components of the device may be made from water vapor permeable materials so as to make the device breathable.

Another aspect of this invention is a pharmaceutical composition for transdermal or transmucosal administration comprising a drug and a permeation enhancing amount of a fatty acid ester or fatty alcohol ether of a $C_2$ to $C_4$ alkanediol where each fatty acid or fatty alcohol portion of the ester or ether is of about 8 to 22 carbon atoms.

Still another aspect of the invention is a method of enhancing the permeation of a body surface to a drug administered to the surface comprising coadministering to the surface a permeation enhancing amount of a fatty acid ester or a fatty alcohol ether of a $C_2$ to $C_4$ alkanediol where each fatty acid or fatty alcohol portion of the ester of ether is of about 8 to 22 carbon atoms.

BRIEF DESCRIPTION OF THE DRAWINGS

FIGS. 2 and 3 are graphs of fentanyl flux from the devices described in Examples 16 and 19, respectively, versus time.

MODES FOR CARRYING OUT THE INVENTION

Figure 1:
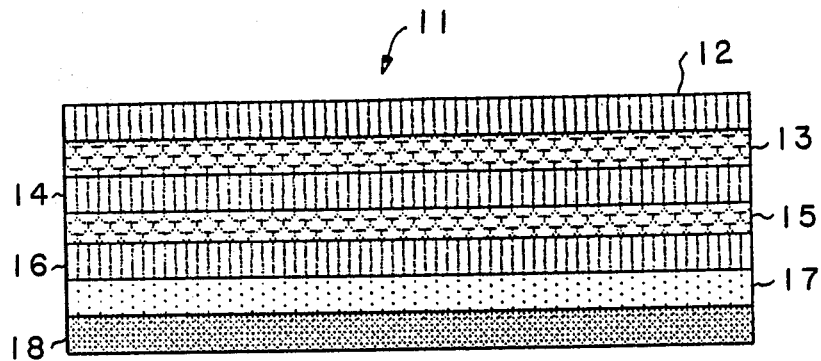
FIG. 1 shows an enlarged sectional view of one embodiment of the transdermal drug-delivery device of the invention.

FIG. 1 shows a device, generally designated 11, which is an embodiment of the invention and is designed for administering a drug, such as estradiol or fentanyl, transdermally at therapeutically effective rates. Device 11 is in the form of a seven-layer laminated composite that is adapted to be adhered to a predetermined area of unbroken skin. The seven layers of the device are: a first structural layer 12 that forms the upper face surface of the device; a hydrophobic viscoelastic polymer layer 13; a second structural layer 14; a second hydrophobic viscoelastic polymer layer 15; a third structural layer 16; a pressure-sensitive adhesive layer 17 which contains the drug; and a release liner layer 18.

Structural layers 12, 14, and 16 are the components of the composite that provide the composite with resiliency and firmness. In this regard, the term "resiliency" denotes the ability of the composite to recover its size and form following deformation. This ability is a function of the thicknesses of the layers, their yield strengths, and their elastic moduli. The term "firmness" is related to the degree of flexibility of the body and is intended to mean that despite its thinness, the composite does not readily and rapidly fold upon itself during normal handling prior to application to the skin. Resiliency permits the composite to be worn comfortably on areas of the skin, such as joints or other points of flexure, that are normally subjected to mechanical strain with little or no likelihood of the composite disengaging from the skin due to differences in the flexibility or resiliency of the skin and the composite. The firmness of the composite lessens the likelihood that the composite will fold upon itself while being handled prior to application to the skin such that portions of its adhesive surface will contact each other and stick together.

One or more of the structural layers may contain drug/enhancer, provided same does not impair the structural integrity of the layer(s) or their mechanical properties.

One or more of the structural layers (12, 14, 16), or hydrophobic viscoelastic polymer layers, or combinations thereof may also be used to impart the device with a desirable or necessary degree of occlusivity which in turn causes the area of skin on which the device is placed to become hydrated. In such a role, layers are selected that have levels of water vapor transmissibility that make the device occlusive to the degree required to cause the area of skin to be hydrated. In such instances it is preferable that the device provide at least about 90% hydration, more preferably at least about 95% hydration of the skin, as measured by a dielectric hydration probe available from Dr. Howard Maibach, U.C.S.F., San Francisco, Calif. Such occlusivity is desirable when drugs such as estradiol or other steroids are being administered. If the drug being administered is such that skin hydration is not necessary or desirable, it is preferable to use layers that provide a composite that is "breathable", i.e., transmits water vapor from the skin to the atmosphere. Such breathability contributes to the nonocclusive nature of the composite and lessens the likelihood that the area of skin on which the composite is worn will become irritated. In the case of device 11, the hydrophobic viscoelastic polymer layers 13 and 15 are the principal layers that make the device occlusive. Thus, in devices that need not be occlusive, these layers may be eliminated if not needed as reservoir layers, thus providing a five-layer composite, or replaced with water vapor permeable layers. In nonocclusive embodiments of the device the water vapor transmission rate (WVTR) of the laminated composite is typically in the range of 11–18 $g/m^2$-hr (as measured using an Evaporimeter at normal room temperature and humidity, i.e., 20° C., 60% relative humidity).

The use of a multiplicity of spaced structural laminas has been found to provide better mechanical properties than use of a single structural lamina having a thickness equal to the combined thicknesses of the spaced laminas. Because of this, suitable mechanical properties may be achieved with a thinner composite employing less elastomer.

Examples of resilient elastomers that may be used to form laminas 12, 14, and 16 are polyether block amide copolymers (e.g., PEBAX copolymers), polyethylene methyl methacrylate block copolymers (EMA) such as NUKRELL polymers, polyurethanes such as PELLATHANE or ESTANE polymers, silicone elastomers, and polyester block copolymers that are composed of hard and soft segments (e.g., HYTREL polymers). The laminas 12, 14, and 16 may be made of the same elastomer or different elastomers. Preferably, they are made of the same resilient elastomer. The structural laminas may be dense (i.e., nonporous) or microporous. The individual thickness of each of these layers will normally be in the range of about 10 to 75 microns. Laminas 14 and 16 do not constitute rate controlling barriers to diffusion of either drug or, when present, enhancer to the skin (i.e., the rate of drug/enhancer administration does not depend on the rate of diffusion of drug/enhancer through these laminas). Depending upon the particular elastomer, these laminas have varying degrees of water barrier properties.

Layers 13 and 15 serve: (1) optionally as reservoirs for enhancer and/or drug; (2) as barriers to water vapor transmission; (3) to resist liquid uptake due to the low solubility of water therein; and (4) to provide additional resiliency and elasticity. In preferred embodiments of an estradiol device, these layers contain enhancer and are composed of a pressure-sensitive adhesive material which is permeable to the enhancer and in which the enhancer is less soluble than in the pressure-sensitive adhesive layer. The incorporation of enhancer into these layers prevents back migration of enhancer from the pressure-sensitive adhesive lamina 17. In such embodiments, layers 13 and 15 will normally contain between about 5% and about 15% by weight enhancer based on the total weight of the layer. The thickness of each of layers 13 and 15 will normally be in the range of 50 to 100 microns.

Layers 13 and 15 may be made from the hydrophobic pressure-sensitive adhesive polymers used to make layer 17 (listed below) or other suitable hydrophobic polymers such as styrene-butadiene copolymers. In embodiments in which one or both of these layers serve as drug/enhancer reservoirs, the polymer should be permeable to drug/enhancer. In such instances the polymer will have a diffusion coefficient and exhibit drug/enhancer solubility comparable to those described below with respect to lamina 17.

Lamina 17 is composed of a pressure-sensitive adhesive optionally containing drug and/or enhancer. When a pressure-sensitive adhesive is used in layers 13 and 15, the same or different material may be used in lamina 17. When lamina 17 functions as a drug/enhancer reservoir, the diffusion coefficient of the adhesive material used in lamina 17 to the drug/enhancer and the solubility of the drug/enhancer in the material are such that the polymer is permeable to the drug/enhancer. Polymers having diffusion coefficients (D) greater than about $10^{-14}$ cm$^2$/sec, usually in the range of $10^{-8}$ to $10^{-12}$ cm$^2$/sec (determined from desorption curves described by Baker, R. W. and Lonsdale, H. K., *Controlled Release: Mechanism and Rates* in *Advances in Experimental Medicine and Biology*, Vol. 47, Tanquary, A. C. and Lacey, R. E. Eds, Plenum Press, N.Y., 1974), relative to the drug, the enhancer, or the combination thereof, and in which the solubility of the drug/enhancer is greater than about 1 mg/ml, usually in the range of 1 to 50 mg/ml are suitable. Examples of polymer types that have the required drug/enhancer permeability and desirable adhesiveness are polysiloxanes (silicone polymers such as polydimethylsiloxane and polymethylphenylsiloxane), hydrophobic polyacrylates, plasticized ethylene-vinylacetate copolymers, low molecular weight polyether block amide copolymers (e.g., PEBAX copolymers), polyurethanes, and rubbery polymers such as polyisobutene. Polysiloxanes and polyisobutenes are preferred.

The term "drug" as used to describe the principal active ingredient of the device intends a biologically active compound or mixture of compounds that has a therapeutic, prophylactic or other beneficial pharmacological and/or physiological effect on the wearer of the device. Examples of types of drugs that may be used in the invention device are antiinflammatory drugs, analgesics, antiarthritic drugs, antispasmodics, antidepressants, antipsychotic drugs, tranquilizers, antianxiety drugs, narcotic antagonists, antiparkinsonism agents, cholinergic agonists, anticancer drugs, immunosuppression agents, antiviral agents, antibiotic agents, appetite suppressants, antiemetics, anticholinergics, antihistaminics, antimigraine agents, coronary, cerebral or peripheral vasodilators, hormonal agents, contraceptive agents, antithrombotic agents, diuretics, antihypertensive agents, cardiovascular drugs, opioids, and the like. The appropriate drugs of such types are capable of permeating through the skin either inherently or by virtue of treatment of the skin with a percutaneous absorption enhancer. Because the size of the device is limited for patient acceptance reasons, the preferred drugs are those that are effective at low concentration in the blood stream. Examples of specific drugs are steroids such as estradiol, progesterone, demegestone, promegestone, testosterone and their esters, nitro-compounds such as nitroglycerine and isosorbide nitrates, nicotine, chlorpheniramine, terfenadine, triprolidine, hydrocortisone, oxicam derivatives such as piroxicam, ketoprofen, mucopolysaccharidases such as thiomucase, buprenorphine, fentanyl, fentanyl analogs, naloxone, codeine, dihydroergotamine, pizotiline, salbutamol, terbutaline, prostaqlandins such as misoprostol and enprostil, omeprazole, imipramine, benzamides such as metoclopramide, scopolamine, peptides such as growth releasing factor and somatostatin, clonidine, dihydropyridines such as nifedipine, verapamil, ephedrine, propanolol, metoprolol, spironolactone, thiazides such as hydrochlorothiazide, flunarizine, sydnone imines such as molsidomine, sulfated polysaccharides such as heparin fractions and the salts of such compounds with pharmaceutically acceptable acids or bases, as the case may be. The drug may be either wholly or partly dissolved in the pressure-sensitive adhesive. The loading of drug in the adhesive will depend on the intended lifetime of the device and will usually be in the range of about 1% to 20% by weight, based on the total weight of the mixture.

Since the inherent permeability of the skin to some drugs such as estradiol is too low to permit therapeutic levels of such drugs to pass through a reasonably sized area of unbroken skin, it is necessary to coadminister a percutaneous absorption enhancer with such drugs. Accordingly, a percutaneous absorption enhancer is present in layer 17 along with such drug (and optionally in one or more of layer 12, 13, 14, 15, and 16). In addition to affecting the permeability of the skin to the drug, the enhancer may also increase the solubility of drug in the adhesive and thereby increase the permeability of the adhesive to the drug.

Applicant has found that fatty acid esters (monoester, diester or mixtures thereof) or fatty alcohol ethers (monoether, diether, or mixtures thereof) of $C_2$ to $C_4$ alkanediols, where each fatty acid/alcohol portion of the ester/ether is of about 8 to 22 carbon atoms and is straight or branched chain, preferably straight chain, is saturated or has 1 to 3 sites of olefinic unsaturation and has 0 to 2 hydroxyl groups, are phase compatible with the preferred type of hydrophobic polymer, increase the solubility of estradiol in such polymer, and enhance the permeability of skin to estradiol when coadministered to the skin. Esters and ethers of straight chain alkanediols whose hydroxyl groups are on terminal carbon atoms are preferred. Monoesters and diesters of propylene glycol are particularly preferred. Examples of such esters and ethers are ethylene glycol octanoate, ethylene glycol monolaurate, ethylene glycol dilaurate, ethylene glycol monoeicosanate, ethylene glycol monostearate, ethylene glycol dioleate, ethylene glycol monolinoleate, propylene glycol monolaurate, propylene glycol dilaurate, propylene glycol monopalmitate, propylene glycol monostearate, propylene glycol monooleate, butylene glycol monodecanoate, butylene glycol monolaurate, butylene glycol monopalmitate, butylene glycol monostearate, 2-hydroxyethyloctyl ether, 2-hydroxyethyllauryl ether, 2-hydroxyethylhexadecyl ether, 2-hydroxyethyleicosyl ether, 3-hydroxypropyllauryl ether, 3-hydroxypropyltetradecyl ether, 3-hydroxypropyloctadecyl ether, 4-hydroxybutyldodecyl ether, and 4-hydroxybutyloctadecyl ether. The enhancer is dispersed in the device in amounts that are sufficient to provide functional amounts of enhancer over the intended lifetime of the device. The loading of enhancer in layer 17 will usually be in the range of 2% to 20% by weight, based on the mixture.

It is important to delineate these types of enhancers (i.e., fatty acid esters and others) from solvent-type enhancers (i.e., alcohol, dimethyl sulfoxide, etc.) in that the latter permeate through skin into the circulating blood while the fatty acid ester-type penetrate the skin to interact on that membrane, but do not permeate through the skin (Ritschell, W. A., Angew Chem. International Edition (1969) 8:699). This distinction has also been demonstrated in skin permeation studies using systems manufactured with varying the amount of propylene glycol monolaurate (PGML), as described in the examples. In this regard, the commercial PGML used in the examples was found to contain substantial amounts, i.e., up to 40% by weight, of the dilaurate (PGDL). Commercial PGML may also contain minor amounts (e.g., up to 10% to 15% by weight) of other ingredients, such as methyl laurate or propylene glycol. Thus, as used in the examples the term "PGML" intends such commercial PGML. Using a gas chromatograph method (Hewlett packard Fast Analysis Capillary, cross-linked dimethyl siloxane 12.5 m×0.2 mm ID; injector port 200° C., column oven 70°–200° C. at 20° C./min with initial 2 min hold at 70° C. and final 5 min hold at 200° C., detector 200° C.; helium carrier gas with a total gas flow rate of 18 ml/min; FID detection; attenuation $2\times 10^{-12}$) with a limit of detection less than 50 ng/ml, no PGML permeation across skin was detected.

It will be appreciated that other percutaneous absorption enhancers, such as those taught in U.S. Pat. Nos. 4,379,454 and 4,568,343, may be coadministered with estradiol to enhance the permeability of the skin to the drug. In this regard, the enhancer should be phase compatible (i.e., it should not bloom) with the components of the layer(s) in which it is incorporated, and its volatility at normal wearing temperatures should be such as to permit it to be made into a solid state device Of course, when the invention device is used to administer drugs other than estradiol to which the permeability of the skin is inherently too low to pass therapeutic amounts, the above described esters or ethers or known enhancers (see, for instance, the above mentioned patents and the references cited in the mentioned patents) will be included in the device and coadministered with the drug. Correlatively, when the device is used to administer a drug to which the permeability of the skin is inherently sufficient to pass therapeutic amounts, it is not necessary to coadminister an enhancer. Thus, in a qeneral terms, the inclusion of an enhancer in the device is optional depending upon the particular drug that is being administered.

When layer 17 is the primary reservoir for drug, its thickness will depend upon the intended lifetime of the device. Thicker layers (and hence more drug and, when present, enhancer) will be used to increase the lifetime. In the case of estradiol, the device will typically be designed to have an effective lifetime of about 3 to 14 days; whereas with fentanyl the effective lifetime will be about 1 to 7 days. In estradiol embodiments, the thickness of the reservoir layer will normally be in the range of about 50 to 100 microns, preferably 50 to 75 microns; whereas in fentanyl embodiments it will normally be about 25 to 150 microns thick.

Device 11 does not include means for controlling the rate at which either drug or enhancer is administered to the skin. Instead, in the case of an estradiol or fentanyl device employing PGML as enhancer, estradiol/fentanyl is presented to the skin at rates in excess of that which the treated area of the skin is able to absorb, while PGML is presented to the skin in quantities sufficient to allow necessary skin interaction. The system does not control either the rate of administration of estradiol/fentanyl or PGML. Unlike ethanol, increasing the concentrations and thermodynamic activities of the PGML in the system does not increase estradiol/fentanyl flux appreciably beyond a limiting PGML concentration in the range of 6% to 10% in the adhesive layer. At PGML concentrations equal to or above this level, estradiol/fentanyl skin permeation becomes essentially constant and independent of PGML driving force in the system or estradiol loading above the limiting level necessary to provide equilibrium saturation in all layers and components of the composite.

It should be understood that the concentrations of drug/enhancer in the layers that are specified above are as of the time of manufacture and that these concentrations may change as concentrations reach equilibrium in accordance with solubility parameters.

Prior to use, device 11 includes a release liner layer 18. Just prior to use this layer is stripped off the device to expose layer 17. This material will normally be made from a drug/enhancer impermeable material that is inherently strippable or rendered so by techniques such as silicone or fluorocarbon treatment.

The rate at which drug/enhancer is/are administered from the device to circulation will depend upon the particular drug/enhancer involved and the basal surface area (the area contacting the skin) of the device. In the case of estradiol used to treat postmenopausal symptoms or osteoporosis, the device should provide sufficient supplemental estradiol (in addition to base level in the patient) to yield steady state plasma levels of estradiol in the range of about 20 to 80 pg/ml. In the case of fentanyl used for the relief of post-operative or chronic pain, the device should provide adequate fentanyl to yield steady state plasma levels of fentanyl in the range of about 2 to 10 mg/ml. In vitro tests such as that described in Medical Device and Diagnostic Industry (1985) 8:35–42 may be used to estimate the flux of drug through human cadaver skin from the devices of the invention. The flux of estradiol from device 11 will normally be in the range of 0.05 to 0.4 $\mu g/cm^2/hr$, more usually 0.1 to 0.2 $\mu g/cm^2/hr$. In the case of fentanyl, flux will normally be in the range of 0.2 to 45 $\mu g/cm^2/hr$. The basal surface area of device 11 will usually be in the range of 2.5 to 50 $cm^2$.

Since device 11 has no fluid elements (i.e., it is a solid state device at normal wearing temperatures, i.e., below about 40° C.), it is readily manufactured using conventional casting and laminating techniques. Commercially available films may be used for structural layers 12, 14, and 16 and release liner layer 18. Depending upon the composition of the structural layers, the hydrophobic polymer layers may be solution cast directly on them. Alternatively, the hydrophobic polymer layers may be cast onto temporary release liner layers and then laminated to the structural layers. The pressure-sensitive adhesive is blended with drug and enhancer using suitable solvents and blending equipment and cast onto layer 18. The entire assembly may then be laminated together. Lamination may be accomplished by thermal bonding, solvent bonding or through use of adhesives as is known in the art. Devices of desired basal surface area may be punched or otherwise formed from the thus assembled laminated composite.

The following examples further illustrate the invention. These examples are not intended to limit the invention in any manner. Unless indicated otherwise, proportions referred to in the examples are by weight %.

EXAMPLE 1

A drug-pressure-sensitive adhesive mixture containing 5.0% estradiol (E2), 10% propylene glycol monolaurate (PGML, Scher) (Commercial pGML from Scher contains about 60% propylene glycol monolaurate, 30% propylene glycol dilaurate and 10% methyl laurate), and 85% polydimethyl siloxane (PDMS, Dow Corning Medical Grade Adhesive 355) was dissolved with trichlorotrifluorethane (freon) to provide a 50%-solids solution. A drug-reservoir pressure-sensitive adhesive layer was prepared by casting the drug-polymer solution onto a fluorocarbon-coated polyester film (3M, 1022) using a 150 micron gap Gardner knife. The freon was evaporated to yield a 75 micron thick drug-pressure-sensitive adhesive film. The drug-reservoir pressure-sensitive adhesive film was laminated to an elastic-resilient polyurethane film (25 micron thick Medifilm 426 Schoeller) to form the drug-reservoir laminate (L1).

An occlusive-resilient polyisobutene (PIB, L-100 Exxon, LM-MS Exxon, H-1900 Amoco in a weight ratio of 1:3:1) layer was prepared by solvent casting a PIB solution, containing 90% PIB and 10% PGML and dissolved with hexane to provide 32% total solids, with a 500 micron gap Gardner knife onto a fluorocarbon-coated polyester film (3M, 1022). The hexane was evaporated to yield a 75 micron thick PIB viscoelastic layer. A 25 micron thick Medifilm 426 film was laminated to the PIB layer to form the occlusive resilient laminate (L2).

A 7-layer laminated composite was prepared by first removing the polyester film of the L2 lamina and laminating the exposed PIB layer to the Medifilm 426 surface of an identical L2 lamina (laminating two L2 laminates together). The polyester film of the resultant laminate is then removed and the exposed PIB surface is laminated to the Medifilm 426 surface of the L1 laminate, the polyester film of the L1 laminate serving as the release liner for the 7-layer system.

The final laminated composite was die cut to fit diffusion cells and E2 steady-state flux across human cadaver skin was determined to be 0.15 to 0.17 $\mu g/cm^2/hr$ for the system at 32° C. using the methods described in Medical Device and Diagnostic Industry (1985) 8:35–42. No PGML skin flux could be quantitated using the above-mentioned gas chromatograph method.

The in vitro release of E2 from the 7-layer system was determined, using a reciprocating dissolution apparatus (USP Test Dissolution Method V) at 32° C., to be square-root-time-dependent over 7 days with a total cumulative release of 190 $\mu g/cm^2$ in 7 days (the flux was 14.66 $\mu g/cm^2/hr^{\frac{1}{2}}$). The laminated composite was translucent and resilient, allowing the system to stretch with the stretching of skin when worn. The system was worn continuously for 7 days on points of flexure of the skin (such as the wrist) without disengaging from the skin.

EXAMPLE 2

An occlusive resilient 7-layer laminated composite was prepared as described in Example 1 using 14% PGML in the L1 laminate instead of 10% PGML. In vitro skin flux was determined to be ~0.15 $\mu g/cm^2/hr$.

EXAMPLE 3

An occlusive resilient 7-layer laminated composite was prepared as described in Example 1 but substituting Medifilm 810 for Medifilm 426 and changing E2 content to 2.0% and 5.5% in L1 and L2 respectively. The adhesive layer in L1 is composed of 10% PGML, 4% silicone oil (Medical Fluid 360, Dow Corning) and 84% PDMS. The adhesive layer of L2 is composed of 10% PGML, 4% silicone oil and 80.5% PDMS instead of 10% PGML and 90% PIB.

In vitro skin flux was determined to be approximately 0.14 $\mu g/cm^2/hr$. During a four day wearing study constant plasma levels were found for 20 and 30 cm² laminates to be approximately 25 and 32 pg/ml respectively in postmenopausal female subjects.

EXAMPLE 4

A 5-layer laminated composite was prepared in a manner similar to that described in Example 1. The polyester layer of L2 was removed and the exposed PIB surface laminated to the Medifilm 426 surface of L1, the polyester layer of L1 serving as the release liner of the final laminate.

The final laminate was tested for E2 skin flux as described in Example 1 and determined to be ~0.12 $\mu g/cm^2/hr$.

EXAMPLE 2

A 5-layer laminated composite was prepared in a manner similar to Example 2. The polyester layer of L2 was removed and the exposed PIB surface laminated to the Medifilm 426 surface of L1, the polyester layer of L1 serving as the release liner of the final laminate.

The final laminate was tested for E2 skin flux and determined to be ~0.15 $\mu g/cm^2/hr$.

Constant plasma concentration of E2 occurred over a 7 day wearing of 20 and 30 cm² laminates. Plasma levels were approximately 30 and 45 pg/ml respectively in postmenopausal female subjects.

EXAMPLES 6 AND 7

Occlusive resilient 7-layer and 5-layer devices were prepared as in Examples 1 and 4, but substituting Medifilm 810 (polyether amide film, 25 microns thick) for Medifilm 426. The flux from the 5-layer device was found to be ~0.14 $\mu g/cm^2/hr$.

EXAMPLES 8 AND 9

Occlusive resilient 7-layer and 5-layer devices were prepared as in Examples 6 and 7, but substituting Medifilm 910 (polyethylene methacrylate copolymer, 25 microns thick) for Medifilm 810. The flux from the 5-layer device was found to be ~0.11 $\mu g/cm^2/hr$.

EXAMPLES 10, 11, AND 12

Occlusive resilient laminated composites are prepared as described in Example 1, but substituting progesterone, demegestone, or promegestone for E2 in the drug-reservoir pressure-sensitive adhesive.

EXAMPLES 13, 14 AND 15

Occlusive resilient laminated composites are prepared as described in Example 1 containing 2.5% E2 and 2.5% of either progesterone, demegestone, or promegestone in the drug-reservoir pressure-sensitive adhesive.

EXAMPLE 16

A drug-polymer reservoir containing 3.5% fentanyl base and 96.5% PIB was dissolved in n-hexane to provide 33% solids solution. A drug reservoir lamina was prepared by casting the drug-polymer reservoir solution onto a fluorcarbon-coated polyester film (3M, 1022) using a 190 micron casting blade. The hexane was evaporated to yield a 63 micron thick drug reservoir film. The drug reservoir film was then laminated onto a structural film consisting of 12.5 micron thick polyester film (3M, 1220) such that the polyester film would serve as a release strip to provide the outer backing-structural lamina/drug reservoir lamina composite (L1).

A pressure-sensitive adhesive consisting of 1.5% fentanyl base, 3.5% PGML (Scher) 2.5% silicone oil (100 centistokes, Dow Corning Medical Fluid) and 92.5% amine resistant polydimethylsiloxane (Dow Corning X7-2900) was dissolved with trichlorotrifluroethane (freon) to provide a 50% solution. The adhesive was cast using a 150 micron gap Gardner wet film applicator onto a fluorcarbon-coated polyester film (3M, 1022) and the solvent was evaporated to provide a 75 micron thick contact adhesive layer. The adhesive was laminated onto a second moisture vapor permeable structural support film consisting of 12.5 micron thick Medifilm 428 or 827 such that the polyester film would act as a release strip to provide a structural support/adhesive/-release strip laminate composite (L2).

The fluorocarbon-coated polyester release strip of L1 was removed and the drug-reservoir surface of L1 was laminated to the Medifilm 428 or 827 surface of L2 to provide the final laminated composite with the polyester film of L2 serving as a peelable release strip for the final laminate. The laminate was allowed to equilibrate for a week prior to skin flux evaluation.

Figure 2:
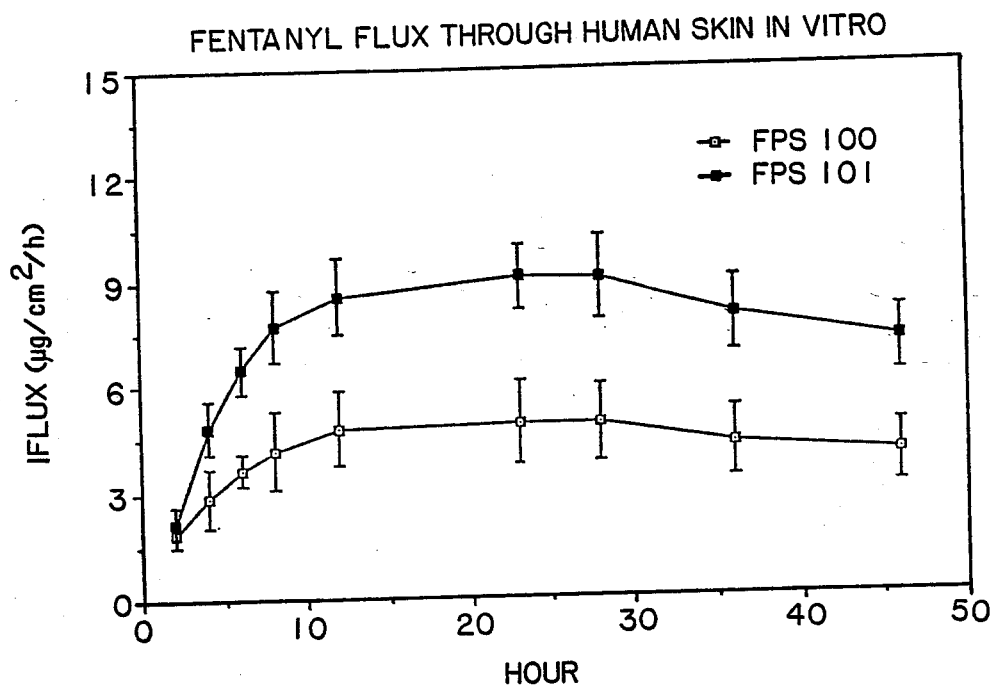

The laminate was die cut to fit diffusion cells and fentanyl base steady state flux through cadaver skin was determined at 32° C. to be 9.7 $\mu g/cm^2/hr$. Fentanyl flux as a function of time is depicted in FIG. 2. Perfect sink condition was maintained by using phosphate buffer (pH=6.0) as a receiver fluid. The cumulative amount of fentanyl base released by in vitro dissolution at 25° C. was square root time dependent over 48 hours (correlation coefficient=0.99, slope 79.4 $g/cm^2/h^{\frac{1}{2}}$), suggesting that diffusion of fentanyl base was under membrane (skin) control.

EXAMPLE 17

A laminated composite was prepared as described in Example 16 except that no structural layer, i.e., Medifilm 827 or 428, was included. Steady-state skin flux of 17.5 $\mu g/cm^2/hr$ was obtained with this device. The fentanyl skin flux was increased two-fold by removal of the Medifilm layer from the laminated composite. This may be due to uptake of PGML as well as fentanyl free base by the Medifilm layer.

EXAMPLE 18

A monolithic device was prepared which consisted of 3.2% fentanyl base, 1.2, 2.5 or 5% of PGML, 2.5% silicone oil and 89.3 to 93.1% of amine resistant polydimethylsiloxane which also acts as an adhesive. Fentanyl concentration was above saturation (i.e., unit thermodynamic activity) in the 1.2 and 2.5% PGML formulations, while in the 5% PGML formulation fentanyl concentration is nearly at saturation. Skin permeation studies were done as described in Example 16. The effect of PGML concentration on the flux of fentanyl through cadaver skin is summarized in the table below.

| % PGML | Fentanyl Skin Flux ($\mu g/cm^2/hr$) | $T_{lag}$ (hr) |
| --- | --- | --- |
| 5.0 | 28.0 | 0.58 |
| 2.5 | 45.5 | 0.51 |
| 1.2 | 22.9 | 0.38 |

As shown, fentanyl flux increases as the concentration of PGML increases from 1.2 to 2.5%, however, flux decreases as the PGML concentration increases to 5%. It appears that at low PGML concentrations the fentanyl skin flux is under solvent control (diffusion layer control) where the flux from saturated solutions increases with increasing concentration of PGML. As the fraction of PGML increased, the flux is under skin control, causing a decrease in fentanyl flux.

EXAMPLE 19

A monolithic device similar to that of Example 18 was prepared using PIB, 0 to 8.6% PGML and 3.5% fentanyl base. Skin permeation studies were done as described in Example 16. Fentanyl skin fluxes from different formulations are depicted in FIG. 3. The effect of PGML concentration on the flux of fentanyl through cadaver skin is summarized in the table below.

| % PGML | Fentanyl base (%) | Fentanyl Skin Flux ($\mu g/cm^2/hr$) | $T_{lag}$ (hr) |
| --- | --- | --- | --- |
| 0 | 2.5 | 8.71 | 0.67 |
| 2.0 | 2.5 | 11.9 | 0.18 |
| 8.6 | 2.5 | 11.8 | <0.1 |
| 5.0 | 5.0 | 15.2 | >0.1 |

It is apparent from these data that fentanyl flux increases 27% (11.9-8.71≈11.9) when 2% PGML is incorporated in the PIB. Nevertheless, the fentanyl flux from the PIB formulation was considerably lower than that from amine resistant polydimethylsiloxane (Example 18). This may be due to lower thermodynamic activity of fentanyl in PIB than in amine resistant polydimethylsiloxane, since fentanyl has a higher solubility in PIB owing to its higher lipophilicity.

EXAMPLES 20 AND 21

Three layer composites were prepared with a drug reservoir lamina consisting of 2.5% fentanyl base 1.5% PGML and 96% acrylate polymer and a pressure-sensitive adhesive consisting of 1.5% fentanyl base, 1.5% PGML, 2.5% silicone oil (100 centistokes) and 94.5% amine resistant polydimethylsiloxane. Acrylate polymer consists of 1 part of Gelva 737 acrylate copolymer and 2 parts of Gelva 788 acrylate polymer (Monsanto). The devices were made either occlusive using flurocarbon-coated polyester film (3M, 1220) as a backing or nonocclusive using 25 micron thick polyether block amide copolymer (Medifilm 827). The nonocclusive device allowed water vapour to be freely transported from the area of the skin on which it was worn to the atmosphere Fentanyl skin flux from the occlusive system was 2.96 $\mu g/cm^2/hr$, whereas the nonocclusive system gave a flux of 0.37 $\mu g/cm^2/hr$. The lower flux of fentanyl from the nonocclusive system is due to the dehydration of skin. Although the fentanyl flux decreased significantly from the nonocclusive system, a steady-state flux of 0.37 $\mu g/cm^2/hr$ was maintained up to 72 hours.

EXAMPLES 22

An adhesive backing containing 2.0% silicone oil (100 centstokes, Dow Corning Medical Fluid) and 92.5% amine resistant polydimethylsiloxane (Dow corning X7-2900) dissolved in trichlorotrifluroethane (freon) to provide a 35% solution was prepared. The adhesive was then laminated onto a structural film consisting of 6.5 micron thick polyester film (3M, 1220) such that the polyester film would provide the outer backing-subassembly (L1).

A drug-containing pressure-sensitive adhesive composition was prepared consisting of 1.8% fentanyl base, 4% PGML, 2.0% silicone oil (100 centstokes, Dow Corning Medical Fluid) and 92.5% amine resistant polydimethylsiloxane (Dow corning X7-2900) dissolved in trichlorotrifluroethane (freon) to provide a 50% solution. The drug-containing pressure-sensitive adhesive composition was cast using a 150 micron gap Gardner wet film applicator onto a fluorocarbon-coated polyester film (3M 1022) and the solvent was evaporated to provide a 75 micron thick contact adhesive layer. A structural support consisting of 12.5 micron thick Cerex film (a nylon spun-bonded nonwoven fabric obtained from James River Corp), was laminated on to the other side of the film of drug-containing pressure-sensitive adhesive composition to form a second subassembly (L2).

The Cerex film surface of L2 was laminated to the adhesive side of L1 to provide the final laminated composite with the fluorocarbon-coated polyester film serving as a peelable release strip for the final laminate. The laminated system was allowed to equilibrate for a week prior to skin flux evaluation.

The laminate system was die cut out to fit diffusion cells and fentanyl base steady state flux through cadaver skin was determined at 32° C. to be 6.5 $\mu g/cm^2/h$. Perfect sink condition was maintained by using phosphate buffer (pH=6.0) as a receiver fluid. The cumulative amount of fentanyl base released by in vitro dissolution at 25° C. was square root time dependent over 48 hours (correlation coefficient=0.99, slope 139.5 $\mu g/cm^2/h^{\frac{1}{2}}$), indicating that diffusion of fentanyl base was under skin control. During 24 hr of skin permeation study 85% of total fentanyl base was delivered and only 15% drug (residual) remained in the composite.

EXAMPLE 23

A three-layer laminated composite for administering fentanyl was prepared in the general manner described in Example 23. It consists of 75 micron thick reservoir layer of 1.8% fentanyl base, 1.2 to 5% PGML, 2.0% silicone oil and 89.3 to 93.1% of amine resistant polydimethylsiloxane which also act as a pressure-sensitive adhesive sandwiched between a 6.5 micron thick polyester backing film (3M, 1220) and a fluorocarbon coated polyester release liner film (3M, 1022). Fentanyl concentration was above saturation (i.e., unit thermodynamic activity). Skin permeation studies were the same as described in Example 22. Fentanyl base steady state flux through cadaver skin was determined at 32° C. to be 7.7 $\mu g/cm^2/h$ with approximately 85% of the fentanyl delivered from the composite after 24 hr.

Modifications of the above-described modes for carrying out the invention that are obvious to those of ordinary skill in the field of transdermal drug-delivery devices and related fields are intended to be within the scope of the following claims.

We claim:

1. A pharmaceutical composition for transdermal or transmucosal administration comprising a nonaqueous mixture of a polymer, a drug and a permeation enhancing amount of a fatty acid ester or fatty alcohol ether of a $C_2$ to $C_4$ alkanediol where each fatty acid or fatty alcohol portion of the ester or ether is of about 8 to 22 carbon atoms.

2. The pharmaceutical composition of claim 1 wherein the composition is in the form of a solid state transdermal drug delivery device.

3. The pharmaceutical composition of claim 2 wherein the drug is estradiol or fentanyl.

4. The pharmaceutical composition of claim 2 wherein the device is a laminated composite of a reservoir layer and a pressure sensitive adhesive layer.

5. The pharmaceutical composition of claim 4 wherein the drug and the fatty acid ester or fatty alcohol ether are both contained primarily in the reservoir layer.

6. The pharmaceutical composition of claim 1 wherein the ester is a monoester and the ether is a monoether.

7. A pharmaceutical composition for transdermal or transmucosal administration comprising a nonaqueous mixture of a polymer, a drug and a permeation enhancing amount of a fatty acid monoester of propylene glycol.

8. The pharmaceutical composition of claim 7 wherein the fatty acid monoester of propylene glycol is propylene glycol monolaurate.

9. The pharmaceutical composition of claim 8 wherein the drug is estradiol or fentanyl.

10. A method of enhancing the permeation of a body surface to a drug administered to the surface comprising coadministering to the surface a permeation enhancing amount of a fatty acid ester or a fatty alcohol ether of a $C_2$ to $C_4$ alkanediol where each fatty acid or fatty alcohol portion of the ester or ether is of about 8 to 22 carbon atoms and wherein said ester or ether is administered from a nonaqueous mixture comprising a polymer and said ester or ether.

11. The method of claim 10 wherein the drug is estradiol or fentanyl.

12. A method of enhancing the permeation of skin to estradiol or fentanyl comprising coadministering to the skin a permeation enhancing amount of propylene glycol monolaurate from a nonaqueous mixture of estradiol or fentanyl, a polymer, and propylene glycol monolaurate.

* * * * *